(12) United States Patent
Isbell et al.

(10) Patent No.: US 6,558,399 B1
(45) Date of Patent: May 6, 2003

(54) DEVICES AND METHOD FOR HANDLING A PLURALITY OF SUTURE ELEMENTS DURING A SUTURING PROCEDURE

(75) Inventors: Lewis Isbell, Santa Clara, CA (US); Jasper Jackson, Newark, CA (US); Katherine Whitin, San Mateo, CA (US)

(73) Assignee: Abbott Laboratories, Abbott Park, IL (US)

( * ) Notice: Subject to any disclaimer, the term of this patent is extended or adjusted under 35 U.S.C. 154(b) by 268 days.

(21) Appl. No.: 09/610,099

(22) Filed: Jun. 30, 2000

(51) Int. Cl.[7] ............................................. A61B 17/04
(52) U.S. Cl. .................................. 606/148; 606/144
(58) Field of Search ............................ 606/144, 148; 139/217, 380; 140/50–52, 33; 112/302

(56) References Cited

U.S. PATENT DOCUMENTS

| | | |
|---|---|---|
| 312,408 A | 2/1885 | Wackerhagen |
| 597,165 A | 1/1898 | Hall |
| 659,422 A | 10/1900 | Shidler |
| 2,127,903 A | 8/1938 | Bowen |
| 2,397,823 A | 4/1946 | Walter |
| 2,588,589 A | 3/1952 | Tauber |
| 2,646,045 A | 7/1953 | Priestley |
| 2,692,599 A * | 10/1954 | Creelman .................. 606/148 |
| 2,959,172 A | 11/1960 | Held |
| 3,033,156 A | 5/1962 | Verbish |
| 3,104,666 A | 9/1963 | Hale et al. |
| 3,470,875 A | 10/1969 | Johnson |
| 3,653,388 A | 4/1972 | Tenckhoff |
| 3,665,926 A | 5/1972 | Flores |
| 3,776,237 A | 12/1973 | Hill et al. |
| 3,820,544 A | 6/1974 | Semm |
| 3,926,194 A | 12/1975 | Greenberg et al. |
| 3,939,820 A | 2/1976 | Grayzel |
| 4,018,228 A | 4/1977 | Goosen |
| 4,109,658 A | 8/1978 | Hughes |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A * | 1/1980 | Gabbay et al. ............. 606/148 |
| 4,216,776 A | 8/1980 | Downie et al. |
| 4,217,665 A | 8/1980 | Bex et al. |
| 4,235,177 A | 11/1980 | Arbuckle |
| 4,317,445 A | 3/1982 | Robinson |
| 4,411,654 A | 10/1983 | Boarini et al. |

(List continued on next page.)

FOREIGN PATENT DOCUMENTS

| | | |
|---|---|---|
| DE | 4219724 C1 | 7/1993 |
| DE | 9217932 | 7/1993 |
| EP | 140557 A2 | 5/1985 |

(List continued on next page.)

OTHER PUBLICATIONS

Elgin National Watch Company, Product Brochure entitled "Elgiloy®, A Cobalt Nickel Spring Alloy," 33 pages.

(List continued on next page.)

Primary Examiner—Julian W. Woo
(74) Attorney, Agent, or Firm—Joseph A. Twarowski

(57) ABSTRACT

A suture handling device for handling a plurality of suture elements is provided. The suture handling device comprises a body. It further comprises a plurality of passages defined on the body. Each passage has a mouth and an opposed end. The passages are arranged to diverge outwardly relative to one another in a direction away from their mouths, such that when the suture handling device is advanced over a plurality of spaced apart suture elements so that the suture elements enter the mouths and pass along the passages, the suture elements become spaced further apart. Advantageously, the suture handling device can be provided with an engaging formation for engaging the suture elements in the slots after they have been spaced further apart, thereby to retain the suture elements on the device.

18 Claims, 4 Drawing Sheets

U.S. PATENT DOCUMENTS

| | | |
|---|---|---|
| 4,412,832 A | 11/1983 | Kling et al. |
| 4,437,465 A | 3/1984 | Nomoto et al. |
| 4,492,229 A | 1/1985 | Grunwald |
| 4,493,323 A | 1/1985 | Albright et al |
| 4,554,543 A | 11/1985 | Amarasinghe |
| 4,586,614 A | 5/1986 | Ger |
| 4,587,969 A | 5/1986 | Gillis |
| 4,596,559 A | 6/1986 | Fleishhacker |
| 4,629,450 A | 12/1986 | Suzuki et al. |
| 4,651,733 A | 3/1987 | Mobin-Uddin |
| 4,723,549 A | 2/1988 | Wholey et al. |
| 4,738,666 A | 4/1988 | Fuqua |
| 4,744,364 A | 5/1988 | Kensey |
| 4,803,984 A | 2/1989 | Narayanan et al. |
| 4,836,205 A | 6/1989 | Barrett |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,926,860 A | 5/1990 | Stice et al. |
| 4,929,246 A | 5/1990 | Sinofsky |
| 4,935,027 A | 6/1990 | Yoon |
| 4,957,498 A | 9/1990 | Caspari et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich e al. |
| 5,021,059 A | 6/1991 | Kensey et al. |
| 5,037,433 A | 8/1991 | Wilk et al. |
| 5,047,039 A | 9/1991 | Avant et al. |
| 5,059,201 A | 10/1991 | Asnis |
| 5,061,274 A | 10/1991 | Kensey |
| 5,078,721 A | 1/1992 | McKeating |
| 5,080,664 A | 1/1992 | Jain |
| 5,100,419 A | 3/1992 | Ehlers |
| 5,100,432 A | 3/1992 | Matsutani |
| 5,109,780 A | 5/1992 | Slouf et al. |
| 5,129,913 A | 7/1992 | Ruppert |
| 5,147,373 A | 9/1992 | Ferzli |
| 5,160,339 A | 11/1992 | Chen et al. |
| 5,171,251 A | 12/1992 | Bregen et al. |
| 5,192,294 A | 3/1993 | Blake, III |
| 5,192,302 A | 3/1993 | Kensey et al. |
| 5,207,703 A * | 5/1993 | Jain .......................... 606/232 |
| 5,219,358 A | 6/1993 | Bendel et al. |
| 5,222,974 A | 6/1993 | Kensey et al. |
| 5,234,443 A | 8/1993 | Phan et al. |
| 5,242,427 A | 9/1993 | Bilweis |
| 5,250,033 A | 10/1993 | Evans et al. |
| 5,250,053 A | 10/1993 | Snyder |
| 5,254,126 A | 10/1993 | Filipi et al. |
| 5,258,003 A | 11/1993 | Ciaglia et al. |
| 5,279,311 A | 1/1994 | Snyder |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,292,309 A | 3/1994 | Van Tassel et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,320,632 A | 6/1994 | Heidmueller |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,353,974 A | 10/1994 | Maurizio |
| 5,354,312 A | 10/1994 | Brinkerhoff et al. |
| 5,364,408 A | 11/1994 | Gordon |
| 5,368,601 A | 11/1994 | Sauer et al. |
| 5,374,275 A | 12/1994 | Bradley et al. |
| 5,376,096 A | 12/1994 | Foster |
| 5,383,896 A | 1/1995 | Gershony et al. |
| 5,385,569 A | 1/1995 | Swor |
| 5,387,221 A | 2/1995 | Bisgaard |
| 5,387,227 A | 2/1995 | Grice |
| 5,395,332 A | 3/1995 | Reesemann et al. |
| 5,395,349 A | 3/1995 | Quiachon et al. |
| 5,397,325 A | 3/1995 | Delia Badia et al. |
| 5,403,329 A | 4/1995 | Hinchcliffe |
| 5,403,338 A | 4/1995 | Milo |
| 5,411,481 A | 5/1995 | Allen et al. |
| 5,413,571 A | 5/1995 | Katsaros et al. |
| 5,417,699 A | 5/1995 | Klein et al. |
| 5,425,705 A | 6/1995 | Evard et al. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schöb et al. |
| 5,454,834 A | 10/1995 | Boebel et al. |
| 5,458,574 A | 10/1995 | Machold et al. |
| 5,470,338 A | 11/1995 | Whitfield et al. |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,665 A | 5/1996 | Fleetwood |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Harnett |
| 5,531,700 A | 7/1996 | Moore et al. |
| 5,540,701 A | 7/1996 | Sharkey et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,554,162 A | 9/1996 | DeLange |
| 5,562,686 A | 10/1996 | Sauer et al. |
| 5,562,688 A | 10/1996 | Riza |
| 5,562,728 A | 10/1996 | Lazarus et al. |
| 5,569,271 A | 10/1996 | Hoel |
| 5,573,540 A | 11/1996 | Yoon |
| 5,591,179 A | 1/1997 | Edelstein |
| 5,591,206 A | 1/1997 | Mourfarrège |
| 5,593,421 A | 1/1997 | Bauer |
| 5,603,718 A | 2/1997 | Xu |
| 5,611,794 A | 3/1997 | Sauer et al. |
| 5,613,974 A | 3/1997 | Andreas et al. |
| 5,613,975 A | 3/1997 | Christy |
| 5,643,289 A | 7/1997 | Sauer et al. |
| 5,669,917 A | 9/1997 | Sauer et al. |
| 5,700,273 A | 12/1997 | Buelna et al. |
| 5,713,910 A | 2/1998 | Gordon et al. |
| 5,716,369 A | 2/1998 | Riza |
| 5,720,757 A | 2/1998 | Hathaway et al. |

| | | | | | |
|---|---|---|---|---|---|
| 5,728,151 A | 3/1998 | Garrison et al. | EP | 669101 B1 | 9/1999 |
| 5,741,276 A | 4/1998 | Poloyko et al. | FR | 1059544 | 7/1952 |
| 5,741,280 A | 4/1998 | Fleenor | JP | 2119866 A | 5/1990 |
| 5,759,188 A | 6/1998 | Yoon | JP | 542161 A | 2/1993 |
| 5,766,183 A | 6/1998 | Sauer | SU | 993922 | 2/1983 |
| 5,766,186 A | 6/1998 | Faraz et al. | SU | 1093329 | 5/1984 |
| 5,779,719 A | 7/1998 | Klein et al. | SU | 1174036 | 8/1985 |
| 5,792,151 A | 8/1998 | Heck et al. | SU | 1544383 | 2/1990 |
| 5,799,661 A | 9/1998 | Boyd et al. | SU | 1648400 | 5/1991 |
| 5,810,850 A | 9/1998 | Hathaway et al. | SU | 820810 | 6/1997 |
| 5,817,113 A | 10/1998 | Gifford, III et al. | WO | WO 94/05213 | 3/1994 |
| 5,820,631 A | 10/1998 | Nobles | WO | WO 94/27503 | 12/1994 |
| 5,824,010 A | 10/1998 | McDonald | WO | WO 94/28801 | 12/1994 |
| 5,836,955 A | 11/1998 | Buelna et al. | WO | WO 95/05121 | 2/1995 |
| 5,836,956 A | 11/1998 | Buelna et al. | WO | WO 95/35065 | 12/1995 |
| 5,846,253 A | 12/1998 | Buelna et al. | WO | WO 97/03613 | 2/1997 |
| 5,848,714 A | 12/1998 | Robson et al. | WO | WO 97/10764 | 3/1997 |
| 5,860,990 A | 1/1999 | Nobles et al. | WO | WO 97/13461 | 4/1997 |
| 5,860,991 A | 1/1999 | Klein et al. | WO | WO 97/17901 | 5/1997 |
| 5,902,311 A | 5/1999 | Andreas et al. | WO | WO 97/20505 | 6/1997 |
| 5,904,697 A | 5/1999 | Gifford, III et al. | WO | WO 00/12013 | 3/2000 |
| 5,951,590 A | 9/1999 | Goldfarb | | | |
| 5,954,732 A | 9/1999 | Hart et al. | | | |
| 5,972,030 A | 10/1999 | Garrison et al. | | | |
| 6,036,699 A | 3/2000 | Andreas et al. | | | |
| 6,048,351 A | 4/2000 | Gordon et al. | | | |
| 6,117,144 A | 9/2000 | Nobles et al. | | | |

FOREIGN PATENT DOCUMENTS

| | | |
|---|---|---|
| EP | 207545 A1 | 1/1987 |
| EP | 0474887 A1 | 3/1992 |
| EP | 478358 A1 | 4/1992 |
| EP | 542126 A3 | 5/1993 |
| EP | 568098 A2 | 11/1993 |
| EP | 589409 A1 | 3/1994 |
| EP | 624343 A2 | 11/1994 |
| EP | 669103 A1 | 8/1995 |
| EP | 568098 B1 | 10/1997 |
| EP | 669102 B1 | 10/1998 |

OTHER PUBLICATIONS

Faulkner, Catherine B., Letter regarding "VasoSeal Vascular Hemostasis," *Datascope*, New Jersey, 1 page only.

Laurus Medical Corporation, "Endoscopic Suturing Made Simple," The Laurus ND–2600 Needle Driver, Irvine, CA., 1 page.

Product Brochure, Laurus Medical Corporation, Irvine, CA "The Laurus In–Line Endoscopic Suturing Device" (Oct. 1994) 1 page.

Rema–Medizintechnik GmbH, Product Brochure entitled "REMA," 7 pages.

Sutura™, "A New Choice In Vascular Suturing . . . ," Let Sutura Show You—TCT Booth 846, Fountain Valley, CA; www.suturainc.com, 1 page only.

* cited by examiner

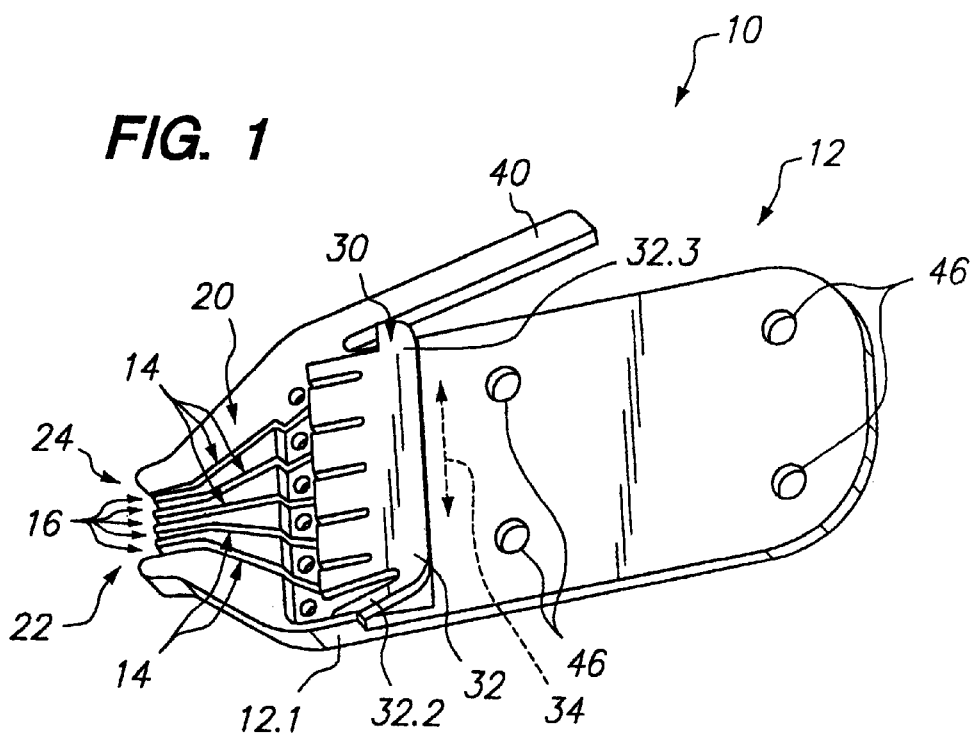
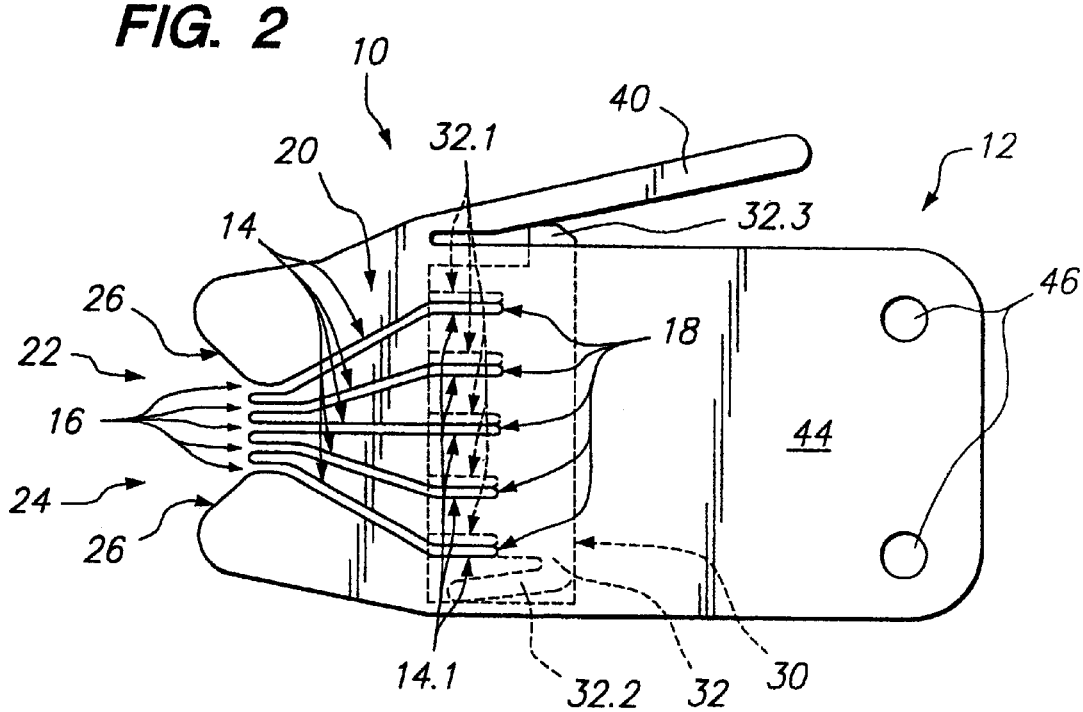

DEVICES AND METHOD FOR HANDLING A PLURALITY OF SUTURE ELEMENTS DURING A SUTURING PROCEDURE

BACKGROUND OF THE INVENTION

This invention relates to handling, or managing, a plurality of suture elements during a surgical procedure.

During many different surgical procedures it is required to join, or secure, patient tissue together. One way often employed by surgeons, or medical assistants, or the like, to secure patient tissue together, is by using suture elements in a suturing procedure. During such a suturing procedure, suture elements are typically located, or placed, at a surgical site on a patient body and opposed portions of the suture elements are then tied to form sutures, or stitches, at the surgical site so as to secure the patient tissue together. Traditionally, such suturing procedures have been performed by using suture carrying needles to locate one or more suture elements through tissue, pulling the suture elements through the tissue to bring the tissue together and then tying opposed portions of the suture elements together to secure the tissue together.

Multi-suture deployment devices have been proposed by means of which a plurality of suture elements can be located, or placed, at a surgical site on a patient body generally at the same time. When such a plurality of suture elements have been located at the surgical site in this fashion, opposed portions of the suture elements are typically extended from the surgical site and then opposed portions of each suture element are typically tied together to secure the tissue together at the surgical site.

It has been found that managing opposed portions of a plurality of suture elements after having been located on the patient body can be rather tedious. In particular, if appropriate care is not taken, the opposed portions of the suture elements can become mixed up, or twisted, so that identifying which portion of a suture element corresponds with which opposed portion of the same suture element becomes a rather arduous task. Furthermore, after the suture elements have been located on the patient body, the opposed portions of the suture elements are typically positioned to extend from the patient body while being carried on suture holders of the multi-suture deployment device. In such a case, the suture elements can be laterally spaced quite close to one another, making manual pick-up of individual suture element portions, so as to tie them together, for example, rather difficult. Naturally, should the opposed portions of the suture elements become mixed up, or should the opposed portions be spaced laterally relatively close together making manual pick up difficult, the suturing procedure can be complicated and can take longer than it would otherwise.

It would be advantageous to provide a device and method whereby the handling of multiple suture elements, during a suturing procedure comprising the placement of a plurality of suture elements on a patient body, generally at the same time, before tying opposed portions of each suture element together, could be made easier at least to reduce the problems set forth above.

SUMMARY OF THE INVENTION

Accordingly, the invention provides a device and method of handling a plurality of suture elements after having been located at a surgical site on a patient body, so as to inhibit opposed portions of the suture elements from becoming mixed up during a suturing procedure and to increase a lateral spacing between the suture elements.

In accordance with one aspect of the invention, there is provided a suture handling device. The suture handling device comprises a body and a plurality of passages defined on the body. Each passage has a mouth and an opposed end. The passages are arranged to diverge outwardly relative to one another in a direction away from the mouths and toward their opposed ends, such that when the suture handling device is advanced laterally over a plurality of spaced apart suture elements so that the suture elements enter the mouths and pass along the passages toward the opposed ends, the suture elements become spaced further apart.

By passing the suture handling device laterally over a plurality of spaced apart suture elements and advancing the suture handling device such that the suture elements travel along the passages, a lateral spacing between the suture elements can be increased. By increasing the lateral spacing in this fashion, manual pick up of opposed portions of the suture elements so as to tie them together can be made easier.

The suture handling device may comprise an engaging formation arranged to engage the suture elements when at the ends of the passages.

The engaging formation may comprise a slide on the body. The slide may be displaceable laterally relative to the passages between an engaging condition, in which the slide protrudes into the passages to engage the suture elements in the passages, and a disengaging condition, in which the slide is clear of the passages to be disengaged from the suture elements.

Accordingly, after the suture elements have passed along the passages so as to increase their lateral spacing, the suture elements can be held captive on the device by means of the engaging formation. Individual suture element portions can then be removed from the device so as to tie them together, while the rest of the suture element portions remain engaged in the passages on the device, thereby inhibiting the suture element portions from becoming mixed up.

In accordance with another aspect of the invention, there is provided a method of handling a plurality of suture elements. The method comprises locating a plurality of suture elements on a patient body, positioning the suture elements in a suture handling device and causing the suture handling device to displace the suture elements laterally away from one another to increase a lateral spacing between the suture elements.

Positioning the suture elements in the suture handling device may comprise passing the suture elements laterally through mouths of passages defined on the suture handling device. The passages can typically diverge laterally away from one another in a direction away from the mouths, so that, causing the suture handling device to displace the suture elements laterally away from one another to increase a lateral spacing between the suture elements comprises advancing the suture elements along the passages such that the suture handling device causes the suture elements to displace laterally away from one another as the suture elements are advanced along the passages.

The method may further comprise positioning opposed portions of a suture element in each passage of the suture handling device and selectively removing the opposed portions of the suture elements from the suture handling device and tying them together to form a plurality of sutures on the patient body.

Locating the plurality of suture elements on the patient body may comprise locating the suture elements through patient tissue such that opposed portions of each suture element extend from the patient tissue.

Locating the plurality of suture elements through patient tissue may comprise actuating a multi-suture deployment device to locate the plurality of suture elements through the patient tissue and withdrawing the multi-suture deployment device from the patient tissue while opposed portions of each suture element is carried on the multi-suture deployment device so that the opposed portions of the suture elements extend from the patient tissue.

Passing the suture handling device laterally across the suture elements may comprise positioning both opposed portions of each suture element in a separate one of the passages of the suture handling device. The method may further comprise selectively removing the opposed portions of each suture element from the suture handling device and tying the opposed portions together.

BRIEF DESCRIPTION OF THE DRAWINGS

The invention will now be described, by way of example, with reference to the accompanying diagrammatic drawings, in which:

FIG. 1 shows a schematic three-dimensional view of part of a suture handling device in accordance with the invention, a cover of the suture handling device having been removed;

FIG. 2 shows a schematic plan view of the suture handling device of FIG. 1, an engaging formation on the suture handling device being in an engaging condition;

DESCRIPTION OF PREFERRED EMBODIMENTS

Figure 3:
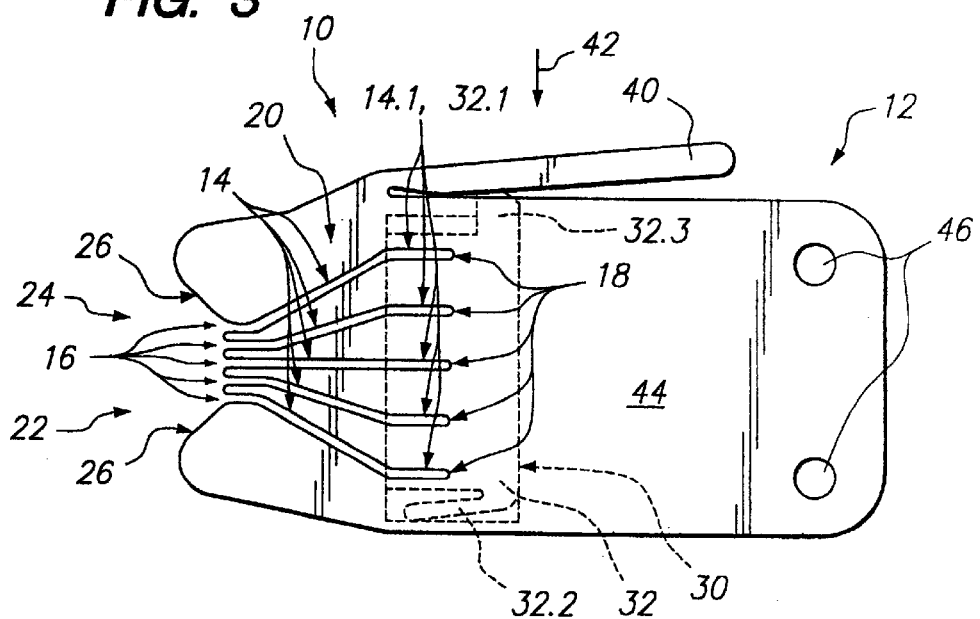
FIG. 3 shows a schematic plan view corresponding to FIG. 2, the engaging formation being in a disengaging condition.

Referring to FIG. 1 of the drawings, part of a suture handling device in accordance with the invention is generally indicated by reference numeral 10. In FIG. 1, a cover of the device 10 has been removed to show the operation of an engaging formation of the device 10, as will be described in greater detail hereinbelow.

The device 10 comprises a body generally indicated by reference numeral 12. The body 12 typically includes the cover, which is not shown in FIG. 1. The device 10 further comprises a plurality of passages 14 defined on the body 12. Each passage 14 has a mouth 16 and an opposed end 18, as can best be seen with reference to FIGS. 2 and 3 of the drawings. The passages 14 are arranged to diverge outwardly relative to one another in a direction away from the mouths 16, as indicated at 20.

The mouths 16 of the passages 14 are typically adjacent one another at an end 22 of the body 12. A guide formation, generally indicated by reference numeral 24 at the end 22 of the body 12 for guiding suture elements laterally into the mouths 16 of the passages 14 is typically provide. The guide formation 24 typically comprises opposed edges, or surfaces, 26, 26 which taper, or converge, toward the mouths 16 so as to assist in guiding suture elements into the mouths 16. The passages 14 typically define portions 14.1 which extend generally parallel relative to one another generally at the ends 18 opposed from the mouths 16.

The device 10 further comprises an engaging formation, generally indicated by reference numeral 30, arranged to engage the suture elements in the passages 14 when the suture elements are generally at the ends 18, or within the generally parallel portions 14.1. The engaging formation 30 typically comprises a slide 32 on the body 12 for selectively providing interference in the passages 14 to enable suture elements to be held captive in the passages 14. The slide 32 is displaceable laterally relative to the passages 14, as indicated by arrow 34 in FIG. 1, and between an engaging condition, in which the slide 32 protrudes into the passages 14 to engage the suture elements in the passages 14, as can be seen with reference to FIG. 2, and a disengaging condition, in which the slide 32 is clear of the passages 14 to be disengaged from the suture elements, as can best be seen with reference to FIG. 3 of the drawings. To this end, the slide 32 comprises a plurality of slots 32.1. When in a disengaging condition, as indicated in FIG. 3, the slots 32.1 are in register with the ends 18 of the passages 14. When in an engaging condition, the slide 32 is laterally displaced such that the slots 32.1 are offset relative to the ends 18 of the passages 14 so as to capture suture element portions within the slots 14.

The slide 32 is typically biased into its engaging condition, as indicated in FIG. 2. To this end, the slide 32 comprises a resilient biasing member 32.2, such as a leaf spring formation, for resiliently urging the slide 32 away from a wall 12.1 of the body 12 and into its engaging condition. A manually operable actuator, such as a lever arm 40, operatively associated with the slide 32, is provided so as to enable the slide 32 to be displaced into its disengaging condition in response to actuating the actuator 40 manually. To this end, the slide 32 typically comprises a protrusion 32.3 which abuts against the actuator 40. Accordingly, when the actuator 40 is displaced toward the body 12, as indicated by arrow 42 in FIG. 3 of the drawings, the slide 32 is displaced laterally relative to the body 12 against the bias of the biasing member 32.2. Advantageously, the device 10 can be provided with a locking arrangement for locking the slide 32 in its engaging condition so as to inhibit accidental displacement of the slide 32 and release of suture elements when engaged thereby. Edges of the slots 14, at least in the region where the slide 32 passes into the slots 14, can be lined with an appropriate material, such as a soft elastomeric material, or the like, to enhance gripping of the suture elements when engaged by the slide 32 in the slots 14 thereby to improve retention of the suture elements when engaged in the slots 14. In addition, or instead, edges of the slide 32 at the slots 32.1 can be lined with an appropriate material, such as a soft elastomeric material, or the like, to enhance gripping of the suture elements when engaged by the slide 32 in the slots 14 thereby to improve retention of the suture elements when engaged in the slots 14. Instead of the slide 32, the slots 14 can be dimensioned, or provided with resilient formations, such that the suture elements are frictionally engaged in the slots automatically when the suture elements are passed into the slots 14.

In FIGS. 2 and 3, the cover of the device 10 is generally indicated by reference numeral 44. The body 12 is typically formed from of synthetic plastics material. Lugs and corresponding holes 46 are provided on the cover 44 and the rest of the body 12 for securing the cover 44 on the rest of the body 12 in an appropriate manner, such as by means of a press fit, a suitable adhesive, or the like.

Figure 4A:
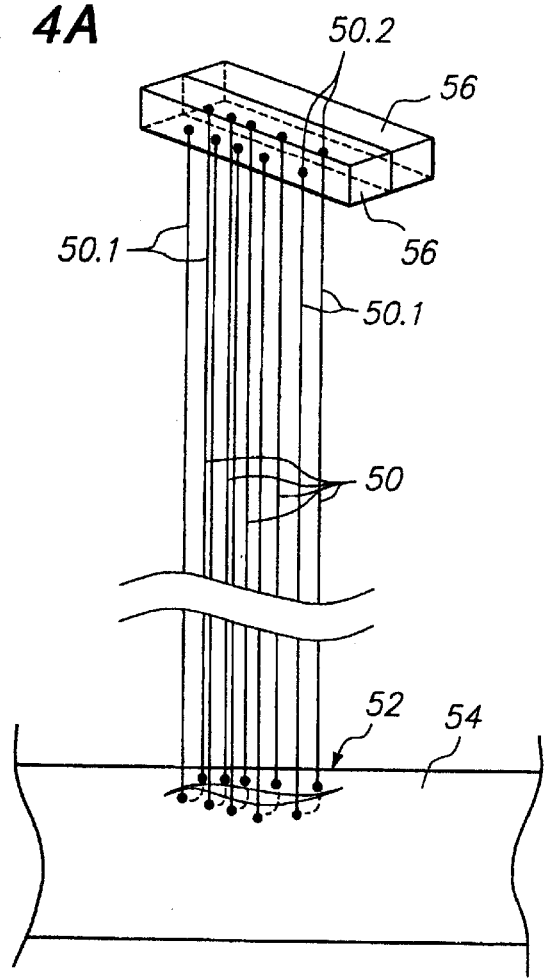
FIG. 4A shows a schematic three-dimensional view of a plurality of suture elements having been located at a surgical site on a patient body by means of a multi-suture deployment device.

Referring to FIG. 4A, a plurality of suture elements 50 are shown as having been located at a surgical site on a patient body. By way of example, the suture elements 50 have been located relative to an incision 52 in a wall of a vessel 54 on the patient body. The suture elements 50 are shown as having been located at the incision by means of a multi-suture deployment device. After location of the suture elements 50 relative to the incision 52 by the multi-suture deployment device, suture holders 56, 56 on which the suture elements are carried are typically extended from the surgical site as shown. It will be seen that opposed portions 50.1 of each suture element 50 are positioned adjacent each other while carried on the holders 56, 56 as indicated at 50.2.

Figure 4B:
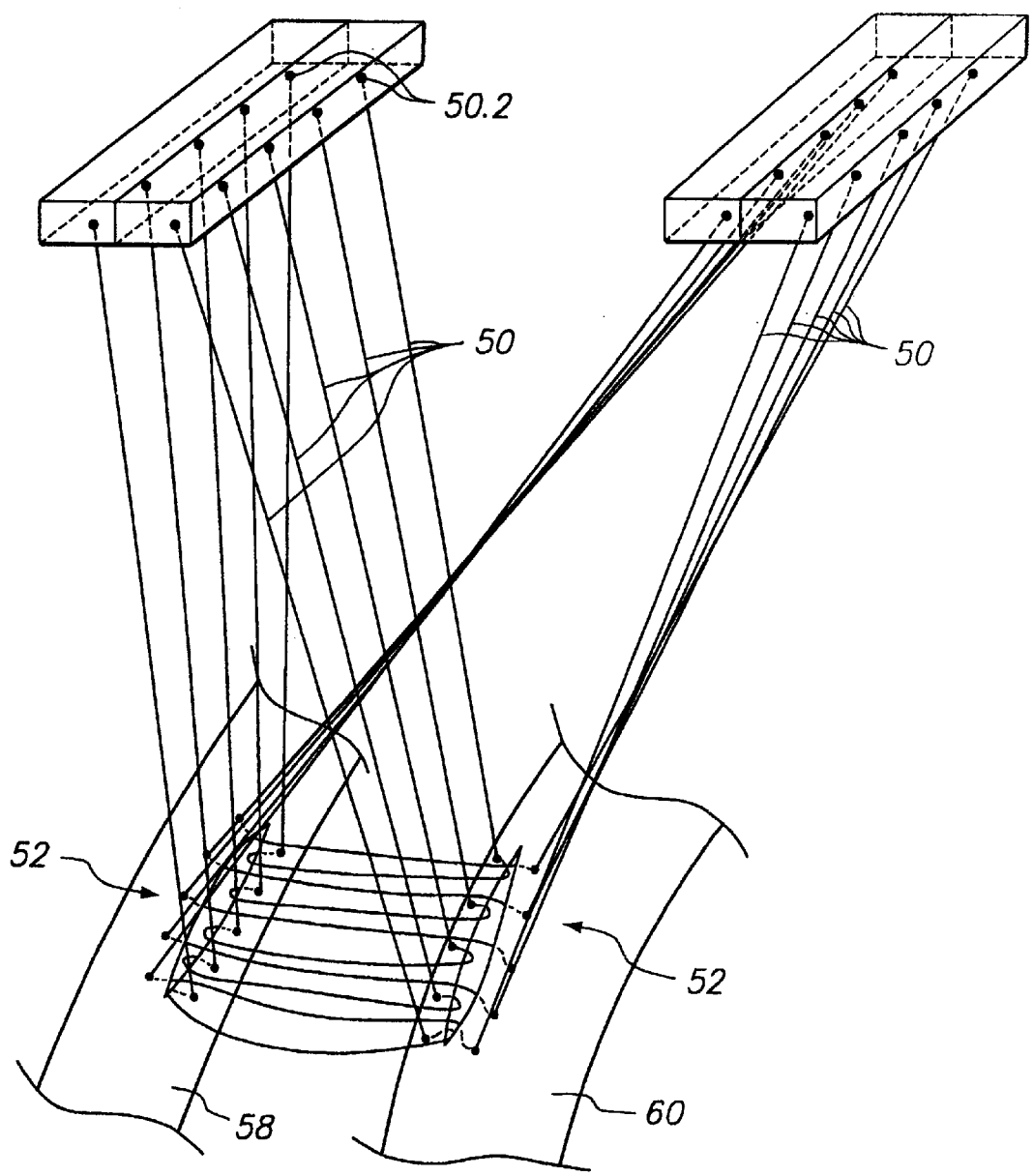
FIG. 4B shows a schematic three-dimensional view of a plurality of suture elements having been located at another surgical site on a patient body by means of a multi-suture deployment device.

Referring now to FIG. 4B, a plurality of suture elements have been located on a patient body so as to perform a side-to-side anastomosis procedure, for example. As in the case shown in FIG. 4A, a plurality of suture elements 50 have been located relative to two incisions 52 of two vessels 58, 60 which are to be sutured together to perform the side-to-side anastomosis, so that blood flowing in one of the vessels 58, 60 can be passed into the other of the vessels 58, 60.

Figure 5:
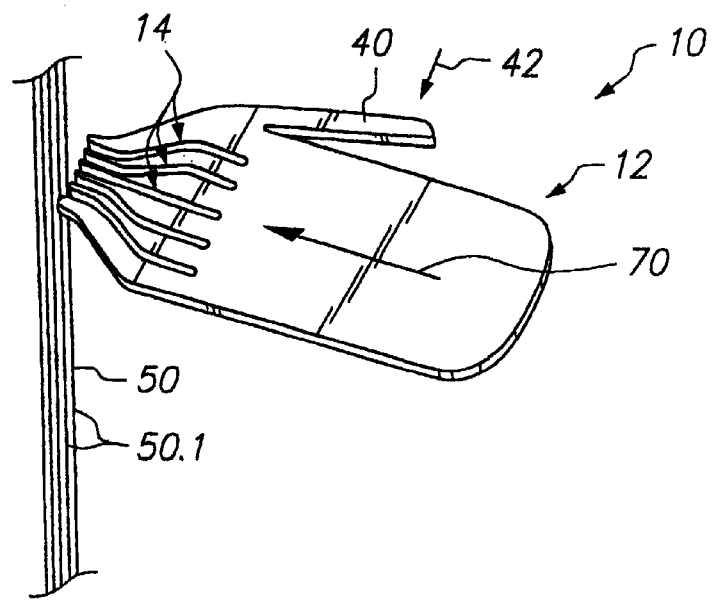
FIG. 5 shows a schematic three-dimensional view of the suture handling device of FIGS. 1 to 3 being advanced laterally over a plurality of spaced apart suture elements so that the suture elements enter mouths and pass along passages defined by the suture handling device toward opposed ends of the passages so that the suture elements become spaced further apart.

Referring now to FIG. 5 of the drawings, after the suture elements 50 have been located on the patient body, as shown in FIGS. 4A and 4B, the device 10 can advantageously be used to facilitate the handling of the suture element portions 50.1 so as to inhibit them from becoming mixed up and to displace the suture elements laterally further apart from one another so as to assist in manual pick up of the suture element portions so as to tie them together. Initially, the device 10 is passed laterally over the suture elements 50 so that the opposed portions 50.1 of each suture element 50 enter the mouths 16 of the passages 14 so as to be positioned in one of the passages 14, as indicated by arrow 70. The converging surfaces 26, 26 assist in guiding the suture elements 50 into the mouths 16. After entering the mouths 16, the device 10 is further advanced laterally over the suture elements 50 to cause the suture elements to pass along the passages 14 so as to become spaced laterally further apart as they pass along the diverging portions of the passages 14.

A spacing between the mouths 16 of the slots 14 typically corresponds to a spacing between adjacent suture elements on the needle holders 56, 56 to enable the suture elements to be readily passed into the mouths 16 of the slots. Accordingly, the device 10 can be arranged to be compatible with a specific suture holder of a specific multi-suture deployment device and can be supplied together with such a multi-suture deployment device.

Figure 6:
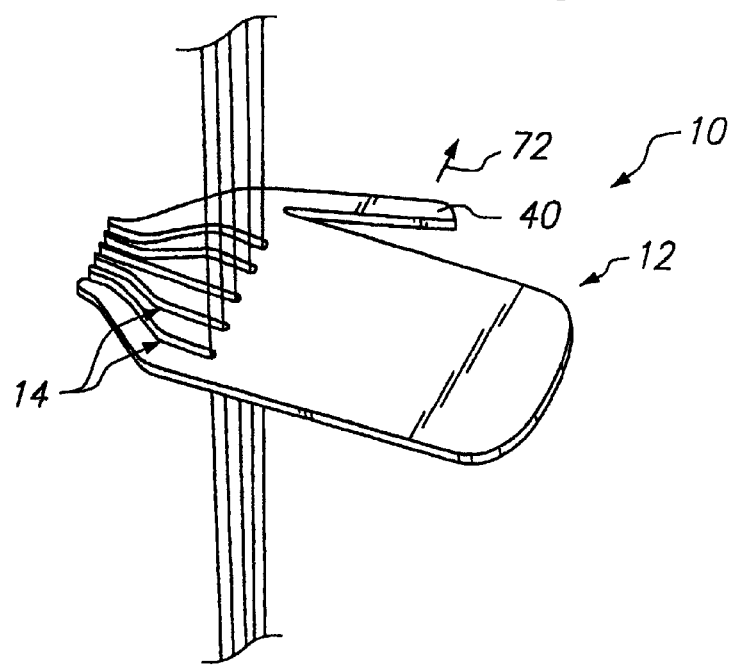
FIG. 6 shows a schematic three-dimensional view corresponding to FIG. 5, after the suture elements have passed along the passages and have been spaced further apart by the suture handling device.

As the device is advanced over the suture elements, the actuator 40 is typically depressed, as indicated by arrow 42, so that the slide 32 is in a disengaging condition to permit the suture elements to pass into and along the parallel portions 14.1 of the passages 14 toward the ends 18. As can best be seen in FIG. 6, and after the suture elements are positioned in the portions 14.1 of the passages 14 at the ends 18, the actuator 40 is typically released, as indicated by arrow 72 in FIG. 5, to permit the urging member 32.2 to urge the slide 32 into its engaging condition so as to engage the suture elements in the passages 14 at the ends 18, thereby releasably to hold the suture elements captive in the passages 14. Conveniently, the device 10 can be provided with a pocket, or the like, so as to enable the holders 56, 56 to be deposited into the pocket after the sutures have been engaged by the device 10, thereby to inhibit the holders 56, 56 from dangling loosely from the device 10.

After the suture element portions 50.1 are engaged on the device 10 in this fashion, opposed portions of each suture element 50 can selectively be removed, or picked up, from the device 10 manually, while the other portions 50.1 remain engaged on the device 10, so that the picked up portions 50.1 can be tied together to form a suture, or stitch, at the surgical site. To remove the portions selectively from the device 10 in this fashion, the portions 50.1 are typically slid along the passages 14 toward the mouths 16 while the slide 32 is in an engaging condition. After the suture elements are engaged on the device 10, the opposed ends at 50.2 of the suture elements 50 can be disengaged from the suture holders 56, 56, or, instead, the ends at 50.2 can be removed from the holders 56, 56 as the portions 50.1 are selectively removed from the device 10.

Conveniently, the device 10 can be mounted on the end of an arm. An opposed end of the arm can be provided with an appropriate mount for mounting the arm on a support normally held at a stationary position relative to the patient body during the suturing procedure. The arm can be bendable to vary the position of the device 10 relative to the support and the patient while the mount is mounted on the support. The arm and mount can be similar to the arm and mount as illustrated in Applicant's co-pending patent application Ser. No. 09 608,832, filed on Jun. 30, 2000 and entitled "Surgical Support Clamp"; the full disclosure of which is incorporated herein by reference. Instead, the device 10 can be provided with an attachment formation for releasably attaching it to an appropriate object during a suturing procedure. For example, the device 10 could be provided with a surface lined with an appropriate adhesive, a spring clip or clamp, a screw clamp, or the like, to enable the device 10 to be releasably attached to an appropriate support, such as, a table, a surgical drape, or the like.

Although an embodiment of the invention has been described in detail above for purposes of clarity and understanding, it will be appreciated that the invention has been described with reference to the above embodiment by way of example only, and that modifications or changes can be made without detracting from the essence of the invention. For example, the suture handling device of the invention could be in the form of a bulldog type clamp having opposed jaws, one of the jaws having diverging slots so that when the sutures are positioned in the slots and the bulldog-type clamp is closed, the sutures are advanced along the diverging slots so as to be spread further apart. Instead of the slide 32, appropriate interference in the slots 14 can be provided by manually snapping a slotted arm into an engaging condition. Devices similar to the devices 10 could be provided which permit separation of the suture elements relative to each other when engaged in the slots. For example, lines of weakness can be provided so that the device can be snapped into several pieces, each carrying a suture element pair so that each pair can be separately loaded into a knot tying device, or the like. Accordingly, the scope of the invention is defined by the appended claims with due regard to equivalents of the claimed elements or features.

What is claimed is:

1. A suture handling device comprising:
   a body; and
   a plurality of passages defined on the body, each passage having a mouth and an opposed end, the passages being arranged to diverge outwardly relative to one another in a direction away from their mouths and toward their opposed ends, such that when the suture handling device is advanced laterally over a plurality of spaced apart suture elements so that the suture elements enter the mouths and pass along the passages toward the opposed ends, the suture elements become spaced further apart.

2. The suture handling device of claim 1, wherein the body is arranged to be held in a user's hand.

3. The suture handling device of claim 1, wherein the mouths of the passages are adjacent one another at an end of the body.

4. The suture handling device of claim 3, wherein the suture handling device comprises opposed surfaces converging toward the mouths so that when the suture handling device is advanced over the suture elements, the converging surfaces serve to guide the suture elements toward the mouths.

5. The suture handling device of claim 3, wherein the passages define portions extending generally parallel relative to one another at their ends opposed from their mouths.

6. The suture handling device of claim 1, which further comprises an engaging formation arranged to engage the suture elements when at the ends of the passages.

7. The suture handling device of claim 6, wherein the engaging formation comprises a slide on the body, the slide being displaceable laterally relative to the passages between an engaging condition, in which the slide protrudes into the passages to engage the suture elements in the passages, and a disengaging condition, in which the slide is clear of the passages to be disengaged from the suture elements.

8. The suture handling device of claim 7, wherein the slide is biased into its engaging condition and the device further comprises a manually operable actuator operatively associated with the slide so as to enable the slide to be displaced into its disengaging condition in response to actuating the actuator.

9. The suture handling device of claim 1, wherein the body is formed of a synthetic plastics material.

10. A method of handling a plurality of suture elements, the method comprising:

locating a plurality of suture elements on a patient body;

positioning the suture elements in a suture handling device; and causing the suture handling device to displace the suture elements laterallyaway from one another to increase a lateral spacing between the suture elements;

wherein positioning the suture elements in the suture handling device comprises passing the suture handling device laterally across the suture elements, wherein the suture handling device comprises a plurality of passages, each passage having a mouth and an opposed end, passing the suture handling device laterally across the suture elements comprising passing the suture elements into the mouths, wherein the passages diverge laterally away from one another in a direction away from their mouths, causing the suture handling device to displace the suture elements laterally away from one another to increase a lateral spacing between one suture element and another comprising advancing the suture elements along the passages such that the lateral spacing between one suture element and another is increased in response to the suture elements being passed along the diverging passages.

11. The method of claim 10, which further comprises engaging the suture elements in the passages after the lateral spacing between the suture elements have been increased.

12. The method of claim 11, wherein engaging the suture elements in the passages comprises causing a slide formation of the suture handling device to displace into an engaging condition, in which the slide formation protrudes into the passages to engage the suture elements in the passages, from a disengaging condition, in which the slide formation is clear of the passages.

13. The method of claim 12, wherein the suture handling device comprises a biasing member which biases the slide formation into its engaging condition, causing the slide formation to displace into its engaging condition comprising permitting the biasing member to displace the slide formation into its engaging condition.

14. The method of claim 13, which comprises displacing the slide formation into its disengaging condition to enable the suture elements to be positioned in the passages so as to be engaged by the slide formation.

15. The method of claim 14, wherein displacing the slide formation into its disengaging condition comprises manually actuating an actuator operatively associated with the slide formation so as to displace the slide formation into its disengaging condition against the bias of the biasing member.

16. The method of claim 10, wherein locating the plurality of suture elements on the patient body comprises locating the suture elements through patient tissue such that opposed portions of each suture element extend from the patient tissue.

17. The method of claim 16, wherein locating the plurality of suture elements through patient tissue comprises actuating a multi-suture deployment device to locate the plurality of suture elements through the patient tissue and withdrawing the multi-suture deployment device from the patient tissue while opposed portions of each suture element is carried on the multi-suture deployment device so that the opposed portions of the suture elements extend from the patient tissue.

18. The method of claim 20, wherein passing the suture handling device laterally across the suture elements comprises positioning both opposed portions of each suture element in a separate one of the passages of the suture handling device, the method further comprising selectively removing the opposed portions of each suture element from the suture handling device and tying the opposed portions together.

* * * * *